US010299844B2

(12) United States Patent
Gauneau et al.

(10) Patent No.: US 10,299,844 B2
(45) Date of Patent: May 28, 2019

(54) OSTEOSYNTHESIS SCREW WITH REDUCED RADIAL COMPRESSION

(71) Applicants: Bertrand Xavier François Gauneau, Dardilly (FR); Eric Stéphane Fourcault, Ecully (FR); Jean-Christophe Alain Giet, Lyons (FR)

(72) Inventors: Bertrand Xavier François Gauneau, Dardilly (FR); Eric Stéphane Fourcault, Ecully (FR); Jean-Christophe Alain Giet, Lyons (FR)

(73) Assignee: IN2BONES, Ecully (FR)

(*) Notice: Subject to any disclaimer, the term of this patent is extended or adjusted under 35 U.S.C. 154(b) by 582 days.

(21) Appl. No.: 14/406,435

(22) PCT Filed: Jun. 25, 2013

(86) PCT No.: PCT/FR2013/051476
§ 371 (c)(1),
(2) Date: Dec. 8, 2014

(87) PCT Pub. No.: WO2014/001705
PCT Pub. Date: Jan. 3, 2014

(65) Prior Publication Data
US 2015/0150613 A1    Jun. 4, 2015

(30) Foreign Application Priority Data

Jun. 26, 2012    (FR) .................................... 12 56066

(51) Int. Cl.
*A61B 17/86*    (2006.01)
(52) U.S. Cl.
CPC ........ *A61B 17/8625* (2013.01); *A61B 17/863* (2013.01); *A61B 17/8605* (2013.01);
(Continued)

(58) Field of Classification Search
CPC ........................... A61B 17/86; A61B 17/8625
See application file for complete search history.

(56) References Cited

U.S. PATENT DOCUMENTS

| | | | | |
|---|---|---|---|---|
| 5,702,445 A | * | 12/1997 | Brånemark | ........ A61B 17/8625 411/387.3 |
| 2004/0147929 A1 | * | 7/2004 | Biedermann | ...... A61B 17/7001 606/266 |

(Continued)

FOREIGN PATENT DOCUMENTS

| | | |
|---|---|---|
| EP | 1 767 160 A2 | 3/2007 |
| WO | WO 97/05830 | 2/1997 |

(Continued)

OTHER PUBLICATIONS

International Search Report, dated Aug. 30, 2013 in connection with PCT International Application No. PCT/FR2013/051476, filed Jun. 25, 2013.

*Primary Examiner* — Christopher J Beccia
(74) *Attorney, Agent, or Firm* — John P. White; Cooper & Dunham LLP

(57) ABSTRACT

The invention concerns an osteosynthesis screw (1) formed from a core (2) externally provided with a helical thread (3), said screw comprising a distal penetration portion and a proximal portion forming the head of the screw (6) and having a conical longitudinal section characterized in that the proximal portion comprises annular notches which are formed in the thickness of the core (2) and in the gaps between the threads of said proximal portion in such a way as to reduce the radial pressure during screwing.—Surgical device.

19 Claims, 2 Drawing Sheets

(52) U.S. Cl.
 CPC ......... *A61B 17/864* (2013.01); *A61B 17/8615* (2013.01); *A61B 17/8635* (2013.01)

(56) References Cited

U.S. PATENT DOCUMENTS

2005/0177243 A1*  8/2005  Lepow ............... A61B 17/8645
                                                               623/21.11
2006/0247642 A1* 11/2006  Stone ................. A61B 17/0642
                                                               623/13.14
2012/0323285 A1* 12/2012  Assell ................ A61B 17/8625
                                                               606/305

FOREIGN PATENT DOCUMENTS

WO    WO 2008/156425 A1    12/2008
WO    WO 2010/099239 A2     9/2010

\* cited by examiner though they are compressive or non-compressive, serv- # OSTEOSYNTHESIS SCREW WITH REDUCED RADIAL COMPRESSION

CROSS-REFERENCE TO RELATED APPLICATIONS

This application is a § 371 national stage of PCT International Application No. PCT/FR2013/051476, filed Jun. 25, 2013, claiming priority of French Patent Application No. 1256066, filed Jun. 26, 2012, the contents of each of which are hereby incorporated by reference in their entirety.

TECHNICAL FIELD

The present invention relates to the technical field of bone surgery, and in particular to osteosynthesis screws in general, which may be compressive or non-compressive, serving to apply compression or merely to stabilize or hold stationary the positioning of bones without compressing them.

The present invention relates to osteosynthesis screws in general, regardless of whether they are compressive or non-compressive, and in particular to a screw formed by a core having an external helical thread, said screw having a distal penetration portion and a proximal portion forming a screw head and having a cross-section that is conical.

PRIOR ART

It is already known to have recourse to osteosynthesis screws that are designed to avoid applying compression to bone masses in which they have been screwed, unlike conventional osteosynthesis screws that provide compression and that a surgeon uses specifically during screw tightening to cause fractured bone portions to move progressively towards each other so as to be put into compression.

In certain surgical situations, it is found to be particularly advantageous to avoid applying compression to bone portions were osteosynthesis is to be assured, where on the contrary all that is required is for the bone fractions to be stabilized, held in place, or prevented from moving.

Thus, once the surgeon has defined the orientations of the bone fractions that are to be repaired and the directions in which they are to be screwed together, the most usual surgical situations involve putting a compression first screw into place that is a compression screw. This screw is put into place in order to ensure good osteo-integration of the bone fractions so as to make it possible to ensure good osteosynthesis.

In such situations, it is found to be particularly advantageous, in order to prevent any danger of the various elements moving relative to one another before bone fusion has occurred or while bone fusion is taking place, to put a second screw into place having the sole purpose of preventing any relative movement of the elements after they have been put into compression.

Osteosynthesis screws that make it possible to perform such a function are osteosynthesis screws that are referred to as being "non-compressive" in so far as they are specially designed to avoid applying compression to bone fractions through which they have been screwed.

As a general rule, known non-compressive osteosynthesis screws have the profile of a cylindrical body of revolution and they are provided with a helical thread extending along their entire length.

Furthermore, in order to make it possible to obtain sufficient material and in order to have sufficient mechanical strength in the screw-driving socket, such screws present a profile that is conical.

Such a profile also makes it easier for the surgeon to control penetration of the osteosynthesis screw in so far as the screw-tightening torque becomes ever greater during screw tightening because of the conical profile of such screws.

Nevertheless, that well-known advantage is accompanied by a drawback associated specifically with the increase in said screw-tightening torque associated with the conical shape, in particular of the head. The head is in danger of causing cracks to appear in the bone mass because of the existence of a high level of radial compression force.

That well-known phenomenon can lead to lines of split being created.

Also known are compression screws that are designed to put bone fragments into compression for osteosynthesis purposes. Those screws may have conical heads that are then liable to generate lines of split just like non-compressive osteosynthesis screws.

SUMMARY OF THE INVENTION

Consequently, the present invention seeks to provide a remedy to the various above-listed drawbacks and to provide a novel osteosynthesis screw that makes it possible to reduce the radial compression of the screw while it is being tightened, and while also limiting the removal of bone mass, but without that weakening the screw.

Another object of the invention is to propose an osteosynthesis screw that is particularly effective and robust.

Another object of the invention is to propose an osteosynthesis screw that is particularly simple to fabricate.

Another object of the invention is to propose an osteosynthesis screw that penetrates particularly easily.

Another object of the invention is to propose an osteosynthesis screw that can be put into place in particularly simple and fast manner.

The objects given to the invention are achieved with the help of an osteosynthesis screw formed by a core provided externally with a helical thread, said screw having a distal penetration portion and a proximal portion forming the screw head and having a conical longitudinal section, the screw being characterized in that the proximal portion includes circular notches that are formed in the thickness of the core and in the inter-thread gaps of said proximal portion so as to reduce radial pressure during screw tightening.

BRIEF DESCRIPTION OF THE DRAWINGS

Other features and advantages of the invention appear and can be seen in greater detail on reading the following description made with reference to the accompanying drawings that are given purely by way of illustrative and non-limiting example, and in which.

BEST MODE OF CARRYING OUT THE INVENTION

In the description and the drawings that follow, reference is made to a non-compressive osteosynthesis screw purely by way of illustrative and non-limiting example, it being understood that the invention may naturally also be applied to a compressive osteosynthesis screw, such that the invention relates to an osteosynthesis screw in general, regardless of whether it is compressive or non-compressive.

Preferably, the screw of the invention is constituted by a non-compressive osteosynthesis screw.

The non-compressive osteosynthesis screw 1 shown in the figures is generally in the form of an oblong screw of substantially cylindrical general shape extending along a longitudinal axis X-X' that also defines the axis about which the screw is turned in order to penetrate into bone mass.

The osteosynthesis screw of the invention is preferably a non-compressive osteosynthesis screw 1, i.e. a screw designed to avoid generating an axial compression force suitable for bringing bone fragments together and putting them under compression once the screw has been caused to pass through them.

In this sense, the non-compressive osteosynthesis screw 1 of the invention is consequently and preferably a screw designed solely to hold, make safe, or prevent changes in the positions of bone fragments that have previously been put under compression by using a conventional compression osteosynthesis screw.

Thus, the non-compressive osteosynthesis screw 1 in accordance with the invention and described below is a screw that is designed for the purpose of avoiding any unwanted relative movements between the bone fragments and masses in which the non-compressive osteosynthesis screw 1 in accordance with the invention is screwed.

As shown in figures, the non-compressive osteosynthesis screw 1 in accordance with the invention comprises a central core 2 that is generally in the form of a substantially cylindrical body of revolution of longitudinally-extending axis X-X' and of section that may be constant or otherwise, said core 2 being hollow or solid.

Figure 4:
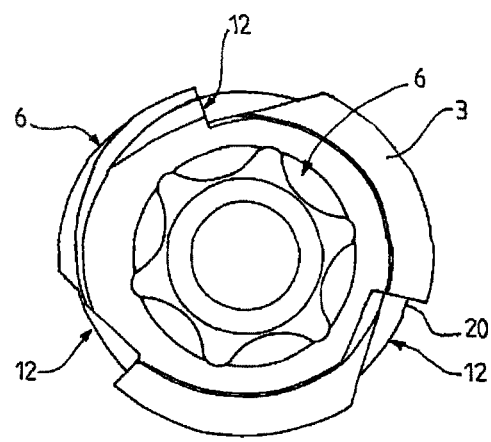
FIG. 4 is an end view showing an embodiment of a non-compressive osteosynthesis screw in accordance with the invention.

When the core 2 is of hollow section, the non-compressive osteosynthesis screw 1 of the invention is a screw with a cannula, as shown in FIG. 4.

In the invention, the non-compressive osteosynthesis screw 1 is made up of the core 2 that is provided externally with a helical thread 3, said screw having a central portion 11 situated between a distal penetration portion 4 and a proximal portion 5 forming the screw head 6 and having a conical longitudinal section, thereby giving it a profile that is conical or substantially conical.

Relative to the axis X-X', the helical thread 3, of pitch that may be constant or otherwise, defines inter-thread gaps 13 of pitch corresponding to the peripheral surface of the core 2.

Figure 1:
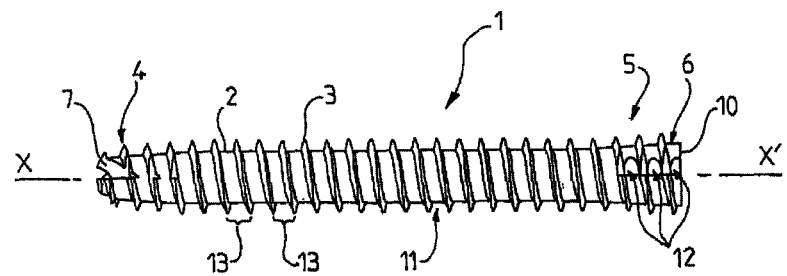
FIG. 1 is a side view showing a non-compressive osteosynthesis screw in accordance with the invention.

In the invention, the distal penetration portion 4 is preferably self-tapping as shown in FIG. 1, and for this purpose it is provided with suitable slots 7 or cutouts.

Preferably, the distal penetration portion 4 presents a diameter that is smaller at the proximal end of the osteosynthesis screw 1 than in the proximity of the central portion 11, so as to improve and facilitate the self-drilling and/or self-tapping action of said osteosynthesis screw 1 while it is being screwed in.

In the invention, the screw head 6 may be made in conventional manner in the form of a "buried" head 6 of section diameter that increases progressively going from the core 2 and the end of the central portion 11 to the terminal end 10 of the proximal portion 5.

Advantageously, the helical thread 3 extends over the entire length of the screw such that the core 2 is covered by the helical thread 3 from the end 10 of the screw head 6 to the end of the distal portion 4, including the central portion 11 of the screw.

As a variant (not shown in figures), the helical thread 3 nevertheless need not extend over the entire length of the screw, for example it may be in the form of two segments, with the central portion 11 not having any threads.

The presence of a screw head 6 with a conical longitudinal section of diameter that increases towards the end 10 and that is of larger diameter than the remainder of the screw makes it possible to obtain good resistance to screw-tightening, thereby enabling the surgeon to control the penetration of the screw as a result of the increasing torque when the screw head 6 penetrates into the bone mass.

Preferably, the screw head 6 is generally of frustoconical shape, in such a manner that its diameter is larger in the proximity of the terminal end 10 and is substantially equal to the diameter of the end of the central portion 11 at the other end of said screw head 6.

According to an important feature of the invention, the proximal portion 5 has circular notches 12 that are made in the thickness of the core 2 in the inter-thread gaps 13 of said proximal portion 5 so as to reduce the radial pressure during screw-tightening.

Thus, in the invention, the presence of circular notches 12 that extend in a direction corresponding to the rotation of the screw and that are formed in the largest-diameter portion of the screw, i.e. in the screw head 6, serves to avoid creating excessive radial pressure in this location since the diameter of the core is reduced in part and from place to place in this zone because of the material that has been removed to create the depression zones that result from the notches 12. This structural feature thus makes it possible to avoid creating lines of split in the bone mass that the screw has passed through, while avoiding making the screw too weak, since it otherwise remains geometrically well-balanced as it penetrates into bone masses.

In the meaning of the invention, the term "circular notches" is used to designate notches that form cavities in the surface of the core 2 in the zone situated between two consecutive threads of the helical thread 3 and that extend generally in the circular direction relative to the circular section of the core 2, as contrasted to longitudinal notches that extend generally in the longitudinal direction of the screw relative to its longitudinally-extending axis X-X'.

Thus, the circular notches 12 form individual cavities, which cavities are arranged in the thickness of the core 2, starting from the periphery of said core 2, and having openings that are directed circumferentially relative to the longitudinally-extending axis X-X' of the osteosynthesis screw 1 (i.e. oriented in a manner that is perpendicular to a radius of the longitudinally-extending axis X-X').

Figure 3:
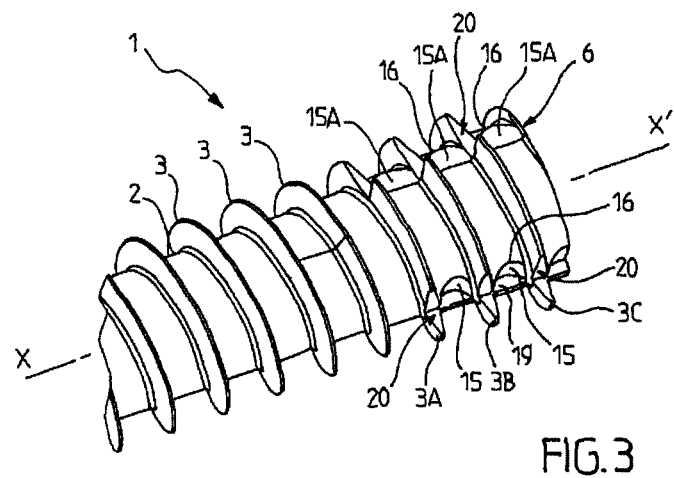
FIG. 3 is a fragmentary perspective view showing an embodiment of a non-compressive osteosynthesis screw in accordance with the invention.

As shown in FIGS. 3 and 4, the osteosynthesis screw 1 of the invention has a plurality of circular notches 12 axially aligned one after another in consecutive inter-thread gaps 13, so as to form at least one row of notches 12.

In the invention, the notches 12 are preferably arranged in the inter-thread gaps 13 created by two adjacent thread portions 3A, 3B, 3C, . . . of the helical thread 3. This procures circular notches 12 that are in regular axial alignment one after another in such a manner that the reduction that is obtained in radial compression is regular and well balanced.

As shown for example in FIG. 3, a row of notches 12 is formed by a plurality of depressions 15A in axial alignment one after another in consecutive or adjacent inter-thread gaps 13.

As a complementary variant, and as shown for example in FIG. 3, the non-compressive osteosynthesis screw 1 of the invention has a plurality of rows of notches 12 that are angularly distributed at regular intervals around the periphery of the core 2.

In a particularly advantageous version of the invention, the notches 12 form depressions 15 with concave curvature (FIG. 3) defining a preferably oval leading edge 16 that is downstream relative to the screw-tightening direction V.

Preferably, the downstream leading edge 16 is a projecting ridge formed by the geometrical intersection between the depression 15 and the core 2, said ridge presenting for example the shape of a portion of a bicylindrical curve or a portion of an elliptical curve having its major radius oriented substantially in the direction of the screw-tightening direction V.

Thus, in the invention, the downstream leading edge 16 is open, thereby facilitating penetration into the bone mass when screwing in the direction V.

Figure 2:
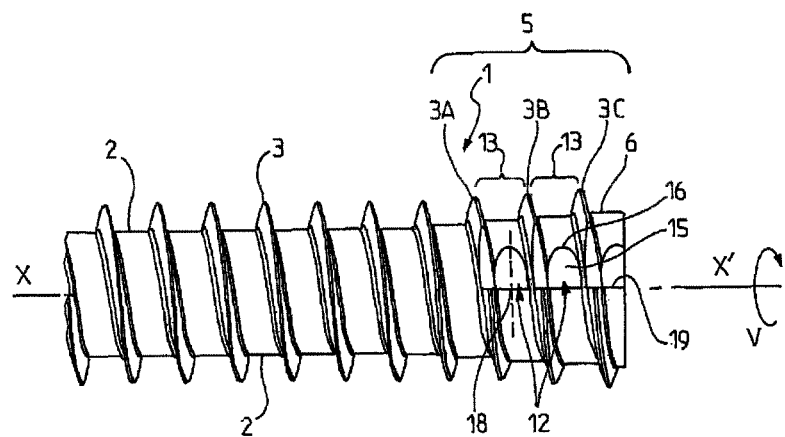
FIG. 2 is an enlarged fragment of FIG. 1 showing an embodiment detail of a non-compressive osteosynthesis screw in accordance with the invention.

As shown, the depression 15 is of elongate shape and presents a longitudinal axis 18 that extends in a midplane substantially parallel to and equidistant from the planes in which two consecutive thread portions 3A, 3B extend (FIG. 2).

In particularly advantageous manner, the depression 15 is provided with an upstream edge 19 that is closed, forming a partition that closes the depression 15.

As shown in FIG. 3 in particular, the upstream edge 19 forms a partition that is orthogonal to the peripheral surface of the core 2. Together, these characteristics thus confer on the screw of the invention good stability during screw tightening because of the good balance of the forces generated and because of the radial pressure that is reduced or even non-existent.

Purely by way of illustration, the non-compressive osteosynthesis screw 1 of the invention may have two or even three rows of circular notches 12, or even more. When the screw of the invention has two rows of circular notches 12, the rows should be angularly offset by 180 degrees, and when the screw of the invention has three rows of circular notches 12, they should be angularly offset by 120 degrees.

By way of complementary variant, as shown in figures, the circular notches 12 are associated with self-tapping cutouts 20 formed in the thickness of the helical thread 3. The cutouts 20 are formed in the thickness of the helical thread 3 and in axial continuity with the associated and adjacent circular notches 12.

This preferred variant embodiment is shown in the figures, and in particular in FIG. 4, which shows the presence of three rows of circular notches 12 that are angularly offset by 120 degrees, the circular notches 12 being associated with L-shaped cutouts 20, preferably right angled cutouts, said cutouts 20 being cut in the thickness of a thread portion 3 in register with the circular notches 12.

Preferably, each of the notches 12 is arranged in the thickness of a thread portion 3 so as to present a first cutting ridge oriented in a manner that is substantially circumferential relative to the longitudinally-extending axis X-X', and a second cutting ridge oriented in a manner that is substantially radial or substantially parallel to a radius of the longitudinally-extending axis X-X', in such a manner that the first and second cutting ridges form an L-shape having its ends situated at the periphery of a thread portion 3.

Nevertheless, in the meaning of the invention, the notches 12 could be formed solely in the thickness of the core 2, and then no cutout 20 is made in the thickness of the helical thread 3, which thread can therefore extend from the proximal portion 5 to the distal portion 4 without any cutout 20.

The osteosynthesis screw 1 of the invention is put into place by the surgeon after the surgeon has previously put a first screw into place that is a compression screw for the purpose of bringing together and applying compression to the bone fragments that are specifically to be fused together by osteosynthesis.

The osteosynthesis screw 1 of the invention is then screwed into the appropriate zone in order to counter any movement of the bone elements and in order to stabilize the elements that the surgeon has put into compression.

Screw-tightening is performed in conventional manner with the help of a screwdriver instrument (not shown), e.g. inserted in the screw head 6, the non-compressive osteosynthesis screw 1 then naturally penetrating into the bone mass because of the self-tapping distal penetration portion 4. The circular notches 12 make it possible to avoid creating excessive radial pressure while the screw is being turned in the direction V, thereby making it possible to preserve a large portion of the bone capital but without that weakening the osteosynthesis screw.

Furthermore, the uniform distribution of notches 12 in the mass of the screw and around it serves to obtain good balance while screw-tightening, leading to regular and controlled penetration of the non-compressive osteosynthesis screw 1 in accordance with the invention.

SUSCEPTIBILITY OF INDUSTRIAL APPLICATION

The invention is susceptible of industrial application in the technical field of bone surgery, and in particular in the field of osteosynthesis screws.

The invention claimed is:
1. An osteosynthesis screw (1) formed by a core (2) provided externally with a helical thread (3), said screw having a distal penetration portion (4) and a proximal portion (5) forming the screw head (6) and having a conical longitudinal section,
   wherein the proximal portion (5) forming the screw head (6) and having the conical longitudinal section includes circular notches (12) that are formed in the thickness of the core (2) and in the inter-thread gaps (13) of said proximal portion (5), said circular notches, as disposed and configured, reducing radial pressure during screw tightening, and
   wherein the circular notches (12) that are formed in the thickness of the core (2) and in the inter-thread gaps (13) of said proximal portion (5) extend generally in a circular direction relative to a circular section of the core (2).
2. The osteosynthesis screw (1) according to claim 1, wherein a plurality of the circular notches (12) are axially aligned one after another in the inter-thread gaps (13) to form at least one row of notches (12).
3. The osteosynthesis screw (1) according to claim 2, wherein the circular notches (12) are provided in adjacent inter-thread gaps (13).

4. The osteosynthesis screw (1) according to claim 2, wherein a plurality of rows of circular notches (12) are angularly distributed at regular intervals around the periphery of the core (2).

5. An osteosynthesis screw (1), formed by a core (2) provided externally with a helical thread (3), said screw having a distal penetration portion (4) and a proximal portion (5) forming the screw head (6) and having a conical longitudinal section,
  wherein the proximal portion (5) forming the screw head (6) and having the conical longitudinal section includes circular notches (12) that are formed in the thickness of the core (2) and in the inter-thread gaps (13) of said proximal portion (5), said circular notches, as disposed and configured, reducing radial pressure during screw tightening, and
  wherein the circular notches (12) form depressions (15) of concave curvature, defining a leading edge (16) that is downstream relative to a screw-tightening direction V.

6. An osteosynthesis screw (1) formed by a core (2) provided externally with a helical thread (3), said screw having a distal penetration portion (4) and a proximal portion (5) forming the screw head (6) and having a conical longitudinal section,
  wherein the proximal portion (5) forming the screw head (6) and having the conical longitudinal section includes circular notches (12) that are formed in the thickness of the core (2) and in the inter-thread gaps (13) of said proximal portion (5), said circular notches, as disposed and configured, reducing radial pressure during screw tightening, and
  wherein the circular notches (12) form depressions (15) of concave curvature, defining a leading edge (16) that is downstream relative to a screw-tightening direction V, each of the depressions (15) being provided with a closed upstream edge (19) forming a partition that is orthogonal to the periphery of the core (2).

7. The osteosynthesis screw (1) according to claim 1, wherein the circular notches (12) are associated with self-tapping cutouts (20) formed in the thickness of the helical thread (3).

8. The osteosynthesis screw (1) according to claim 1, further comprising a cannula.

9. The osteosynthesis screw (1) according to claim 1, wherein the helical thread (3) extends over the entire length of the screw.

10. The osteosynthesis screw (1) according to claim 1, wherein the distal penetration portion (4) is self-tapping.

11. The osteosynthesis screw (1) according to claim 1, wherein said screw is a non-compressive screw.

12. The osteosynthesis screw (1) according to claim 3, wherein a plurality of rows of the circular notches (12) are angularly distributed at regular intervals around the periphery of the core (2).

13. The osteosynthesis screw (1) according to claim 2, wherein the circular notches (12) form depressions (15) of concave curvature, defining a leading edge (16) that is downstream relative to a screw-tightening direction V.

14. The osteosynthesis screw (1) according to claim 3, wherein the circular notches (12) form depressions (15) of concave curvature, defining a leading edge (16) that is downstream relative to a screw-tightening direction V.

15. The osteosynthesis screw (1) according to claim 4, wherein the circular notches (12) form depressions (15) of concave curvature, defining a leading edge (16) that is downstream relative to a screw-tightening direction V.

16. The osteosynthesis screw (1) according to claim 13, wherein the depression (15) is provided with a closed upstream edge (19) forming a partition.

17. The osteosynthesis screw (1) according to claim 6, wherein the circular notches (12) are associated with self-tapping cutouts (20) formed in the thickness of the helical thread (3).

18. The osteosynthesis screw (1) according to claim 17, further comprising a cannula.

19. The osteosynthesis screw according to claim 1, wherein a diameter in the conical longitudinal section including the circular notches formed therein decreases in a direction from the screw head in the proximal portion towards the distal penetration portion.

* * * * *